United States Patent
Wang et al.

(10) Patent No.: US 8,758,756 B2
(45) Date of Patent: Jun. 24, 2014

(54) ANTI-HUMAN EPIDERMAL GROWTH FACTOR RECEPTOR ANTIBODY AND USES THEREOF

(75) Inventors: Hsiang-Ching Wang, Hsinchu (TW);
Ming-Hua Yang, Taipei (TW);
Ling-Mei Wang, Taipei (TW);
Min-Yuan Chou, Taipei (TW);
Jyuan-Jyuan Syu, Pingtung County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/611,291

(22) Filed: Sep. 12, 2012

(65) Prior Publication Data

US 2013/0171174 A1     Jul. 4, 2013

(30) Foreign Application Priority Data

Dec. 28, 2011    (TW) .............................. 100149126 A

(51) Int. Cl.
*C07K 16/30* (2006.01)
*C07K 16/46* (2006.01)
*A61K 39/395* (2006.01)
*C07K 14/71* (2006.01)

(52) U.S. Cl.
USPC ................. 424/143.1; 424/138.1; 424/133.1; 424/155.1; 530/387.3; 530/387.7; 530/388.22; 530/388.8; 530/391.3

(58) Field of Classification Search
None
See application file for complete search history.

(56) References Cited

U.S. PATENT DOCUMENTS

| | | |
|---|---|---|
| 2009/0016957 A1 | 1/2009 | Nilsson et al. |
| 2010/0015124 A1 | 1/2010 | Threadgill et al. |
| 2010/0092470 A1 | 4/2010 | Bhatt et al. |
| 2011/0123529 A1 | 5/2011 | Laeremans et al. |
| 2013/0224207 A1* | 8/2013 | Smith et al. |

FOREIGN PATENT DOCUMENTS

| | | |
|---|---|---|
| WO | WO 2008/141449 A1 | 11/2008 |
| WO | WO 2010/042815 A2 | 4/2010 |

OTHER PUBLICATIONS

Alimandi et al., "Epidermal growth factor and betacellulin mediate signal transduction through co-expressed ErbB2 and ErbB3 receptors", The EMBO Journal, vol. 16, No. 18, 1997, pp. 5608-5617.
Bell et al., "Differential tumor-targeting abilities of three single-domain antibody formats", Cancer Letters, vol. 289, 2010, pp. 81-90.
Ettenberg et al., "cbl-b inhibits epidermal growth factor receptor signaling", Oncogene, vol. 18, 1999, pp. 1855-1866.

(Continued)

*Primary Examiner* — Claire Kaufman
(74) *Attorney, Agent, or Firm* — Birch, Stewart, Kolasch & Birch, LLP

(57) ABSTRACT

An anti-human epidermal growth factor receptor (EGFR) antibody including an amino acid sequence as set forth in SEQ ID No. 3 is provided. The antibody binding to a labeling agent and used for labeling cells is also provided. A novel method for screening an anti-EGFR antibody is further provided.

15 Claims, 14 Drawing Sheets

(56) References Cited

OTHER PUBLICATIONS

Friedman et al., "Phage display selection of Affibody molecules with specific binding to the extracellular domain of the epidermal growth factor receptor", Protein Engineering, Design & Selection, vol. 20, No. 4, 2007, pp. 189-199.

Gottlin et al., "Isolation of Novel EGFR-Specific VHH Domains", Journal of Biomolecular Screening, vol. 14(1), 2009, pp. 77-85.

Heitner et al., "Selection of cell binding and internalizing epidermal growth factor receptor antibodies from a phage display library", Journal of Immunological Methods, vol. 248, 2001, pp. 17-30.

Li et al., "Identification and characterization of a novel peptide ligand of epidermal growth factor receptor for targeted delivery of therapeutics", The Faseb Journal, vol. 19, 2005, pp. 1978-1985.

Lin et al., "A cell-based high-throughput screen for epidermal growth factor receptor pathway inhibitors", Analytical Biochemistry, vol. 377, 2008, pp. 89-94.

Zhao et al., "Selection and characterization of an internalizing epidermal growth-factor-receptor antibody", Biotechnol. Appl. Biochem., vol. 46, 2007, pp. 27-33.

* cited by examiner

```
                                                                              +Majority
     ATGGCCCAGGTGCAGCTGTTGGAGTCTGGGGGAGGCTTGGTACAGCCTGGGGGGTCCCTG              Majority
              10         20         30         40         50         60

1 ATGGCCCAGGTGCAGCTGTTGGAGTCTGGGGGAGGCTTGGTACAGCCTGGGGGGTCCCTG              D2(V1).seq
   1 ATGGCCCAGGTGCAGCTGTTGGAGCTGTGGGGAGGCTTGGTACAGCCTGGGGGGTCCCTG              D2(V2).seq +Majority
     CGTCTCCTGTGCAGCCTCCGGATATAGGTTTAACTCTGAAGGTATATGGGCTGGGTCCGC              Majority
              70         80         90        100        110        120

61 CGTCTCCTGTGCAGCCTCCGGATATAGGTTTAACTCTGAAGGTATATGGGCTGGGTCCGC              D2(V1).seq
  61 CGTCTCCTGTGCAGCCTCCGGATATAGGTTTAACTCTGAAGGTATATGGGCTGGGTCCGC              D2(V2).seq
```

| FIG. 3A |
|---------|
| FIG. 3B |
| FIG. 3C |

```
                                                                              +Majority
                                                                              Majority GTTCCTAGGAGGTATGTGGTGGCTGACTGGTCTGACTGCGAACCGATCAGGTATTGGGGTCAG        D2(V1).seq
                                                                              D2(V2).seq
          310       320       330       340       350       360
   301 GTTCCTAGGAGGTATGTGGTGGCTGGCTGACTGGTCTGACTGCGAACCGATCAGGTATTGGGGTCAG
   301 GTTCCTAGGAGGTATGTGGTGGTGGCTGACTGGTCTGACTGCGAACCGATCAGGATTGGGGTCAG +Majority
                                                                              Majority GGAACCCTGGTCACCG TCTCGAGC                                               D2(V1).seq
                                                                              D1(V2).seq
             370       380
   361 GGAACCCTGGTCACCG TCTCGAGC
   361 GGAACCCTGGTCACCG TCTCGAGC
```

FIG. 3C

SEQUENCE LISTING

<160> NUMBER OF SEQ ID NOS: 7

<210> SEQ ID NO 1
<211> LENGTH: 384
<212> TYPE: DNA
<213> ORGANISM: Homo sapiens

<400> SEQUENCE: 1

| | | | | | |
|---|---|---|---|---|---|
| atggcccagg | tgcagctgtt | ggagtctggg | ggaggcttgg | tacagcctgg | ggggtccctg | 60 |
| cgtctctcct | gtgcagcctc | cggatatagg | tttaactctg | aagctatggg | ctgggtccgc | 120 |
| caggctccag | ggaagggtct | agagtgggta | tcaagcatta | atatgcgagg | cggtagcaca | 180 |
| tactacgcag | actccgtgaa | gggccggttc | accatctccc | gtgacaattc | caagaacacg | 240 |
| ctgtatctgc | aaatgaacag | cctgcgtgcc | gaggacaccg | cggtatatta | ttgcgcgaca | 300 |
| gttcctagga | gtatgtggtg | ggctggtctg | actgcgaagc | cgatcaggta | ttggggtcag | 360 |
| ggaaccctgg | tcaccgtctc | gagc | | | | 384 |

<210> SEQ ID NO 2
<211> LENGTH: 384
<212> TYPE: DNA
<213> ORGANISM: Homo sapiens

<400> SEQUENCE: 2

| | | | | | |
|---|---|---|---|---|---|
| atggcccagg | tgcagctgtt | ggagtctggg | ggaggcttgg | tacagcctgg | ggggtccctg | 60 |
| cgtctctcct | gtgcagcctc | cggatatagg | tttaactctg | aagctatggg | ctgggtccgc | 120 |
| caggctccag | ggaagggtct | agagtgggta | tcaagcatta | atatgcgagg | cggtagcaca | 180 |
| tactacgcag | actccgtgaa | gggccggttc | accatctccc | gtgacaattc | caagaacacg | 240 |
| ctgtatctgc | aaatgaacag | cctgcgtgcc | gaggacaccg | cggtatatta | ttgcgcgaca | 300 |
| gttcctagga | gtatgtggtg | ggctggtctg | actgcgaagc | cgatcaggga | ttggggtcag | 360 |
| ggaaccctgg | tcaccgtctc | gagc | | | | 384 |

<210> SEQ ID NO 3
<211> LENGTH: 128
<212> TYPE: PRT
<213> ORGANISM: Homo sapiens

<400> SEQUENCE: 3

Met Ala Gln Val Gln Leu Leu Glu Ser Gly Gly Gly Leu Val Gln Pro
1               5                   10                  15

Gly Gly Ser Leu Arg Leu Ser Cys Ala Ala Ser Gly Tyr Arg Phe Asn
            20                  25                  30

Ser Glu Ala Met Gly Trp Val Arg Gln Ala Pro Gly Lys Gly Leu Glu
        35                  40                  45

Trp Val Ser Ser Ile Asn Met Arg Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Thr Val Pro Arg Ser Met Trp Trp Ala Gly Leu Thr Ala
            100                 105                 110

Lys Pro Ile Arg Tyr Trp Gly Gln Gly Thr Leu Val Thr Val Ser Ser
        115                 120                 125

<210> SEQ ID NO 4
<211> LENGTH: 128
<212> TYPE: PRT
<213> ORGANISM: Homo sapiens

<400> SEQUENCE: 4

Met Ala Gln Val Gln Leu Leu Glu Ser Gly Gly Gly Leu Val Gln Pro
1               5                   10                  15

Gly Gly Ser Leu Arg Leu Ser Cys Ala Ala Ser Gly Tyr Arg Phe Asn
            20                  25                  30

Ser Glu Ala Met Gly Trp Val Arg Gln Ala Pro Gly Lys Gly Leu Glu
        35                  40                  45

Trp Val Ser Ser Ile Asn Met Arg Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Thr Val Pro Arg Ser Met Trp Trp Ala Gly Leu Thr Ala
            100                 105                 110

Lys Pro Ile Arg Asp Trp Gly Gln Gly Thr Leu Val Thr Val Ser Ser
        115                 120                 125

<210> SEQ ID NO 5
<211> LENGTH: 696
<212> TYPE: DNA
<213> ORGANISM: Homo sapiens

<400> SEQUENCE: 5
gagcccaaat ctggtgacaa aactcacaca tgcccaccgt gcccagcacc tgaactcctg      60
gggggaccgt cagtcttcct cttccccca aaacccaagg acaccctcat gatctcccgg     120
acccctgagg tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagccctcc cagcccccat cgagaaaacc     360
atctccaaag ccaaagggca gccccgagaa ccacaggtgt acaccctgcc cccatcccgg     420
gatgagctga ccaagaacca ggtcagcctg acctgcctgg tcaaaggctt ctatcccagc     480
gacatcgccg tggagtggga gagcaatggg cagccggaga caactacaa gaccacgcct     540 cccgtgctgg actccgacgg ctccttcttc ctctacagca agctcaccgt ggacaagagc     600
aggtggcagc aggggaacgt cttctcatgc tccgtgatgc atgaggctct gcacaaccac     660
tacacgcaga agagcctctc cctgtctccg ggtaaa                                696

<210> SEQ ID NO 6
<211> LENGTH: 224
<212> TYPE: PRT
<213> ORGANISM: Homo sapiens

<400> SEQUENCE: 6

Glu Pro Lys Ser Gly Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

-continued

```
Val Asp Val Ser His Glu Asp Pro Glu Val Lys Phe Asn Trp Tyr Val
    50              55                  60

Asp Gly Val Glu Val His Asn Ala Lys Thr Lys Pro Arg Glu Glu Gln
65              70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

<210> SEQ ID NO 7
<211> LENGTH: 384
<212> TYPE: DNA
<213> ORGANISM: Homo sapiens

<400> SEQUENCE: 7
atggcccagg tgcagctgtt ggagtctggg ggaggcttgg tacagcctgg ggggtccctg      60
cgtctctcct gtgcagcctc cggatatagg tttaactctg aagctatggg ctgggtccgc     120
caggctccag ggaagggtct agagtgggta tcaagcatta atatgcgagg cggtagcaca     180
tactacgcag actccgtgaa gggccggttc accatctccc gtgacaattc caagaacacg     240
ctgtatctgc aaatgaacag cctgcgtgcc gaggacaccg cggtatatta ttgcgcgaca     300
gttcctagga gtatgtggtg ggctggtctg actgcgaagc cgatcaggta ttggggtcag     360
ggaaccctgg tcaccgtctc gagc                                            384
```

ANTI-HUMAN EPIDERMAL GROWTH FACTOR RECEPTOR ANTIBODY AND USES THEREOF

CROSS REFERENCE TO RELATED APPLICATIONS

This application claims the priority of Taiwan Patent Application No. 100149126, filed Dec. 28, 2011, which is incorporated herein by reference.

INCORPORATION BY REFERENCE OF SEQUENCE LISTING

A sequence listing submitted as a text file via EFS-Web is incorporated herein by reference. The text file containing the sequence listing is named "0965-A23833-US_Seq_Listing.txt"; its date of creation is Mar. 8, 2012; and its size is 6,681 bytes.

TECHNICAL FIELD

The technical field relates to an anti-human epidermal growth factor receptor (EGFR) antibody and uses thereof.

BACKGROUND

The epidermal growth factor receptor (EGFR) belongs to the ErbB family of receptor tyrosine kinases (RTK). Upon ligand binding, EGFR stimulates downstream cell signaling cascades that influence cell proliferation, migration, apoptosis, and survival. The two FDA-approved anti-EGFR antibodies, chimeric monoclonal antibody (mAb) Cetuximab (Erbitux™) and fully human mAb Panitumumab (Vectibix™), are high-affinity mAbs with therapeutic applications in cancers of the colon and head & neck (Wheeler et al. 2010, *Nat Rev Clin Oncol*. 7, 493-507). Due to the higher specific and affinity as comprised with peptide ligand or small molecular, antibodies not only used for therapy but also used as vectors to deliver drugs into the target cells.

Despite the success of IgG, such as Cetuximab and Panitumumab, used in clinical trials, a large size of IgG (~150 kDa) may affect the tumor penetration (Jain et al. 2005, *Cancer Res*. 65, 7840-6). Many kinds of antibody formats, such as single chain variable fragments (scFvs) and scFv fused with Fc domain (scFv-Fc), have been engineered to improve tumor penetration. The naturally devoid of light chain antibodies of camels and llamas provide new perspectives in the antibody engineering area (Hamers-Casterman et al. 1993, *Nature*, 363, 446-8.). Single-domain antibodies (sd-Abs, also called dAbs) are the smallest antigen binding fragment based on a single variable domain of human antibodies and are highly soluble when expressed in a recombinant system (Jespers et al. 2004, *Nat Biotechnol*. 22, 1161-5.). Recently, a reference protocol for phage display selection of human antibody fragment via filamentous bacteriophage was set up (Lee et al. 2007 *Nat Protoc*. 2, 3001-8.). For enhancing the hit rates, the phage display selection based on antigen expressing cells, to mimic the physiological form of receptors, has also been reported in the literature (Heitner et al. 2001 *J Immunol Methods*. 248, 17-30). The EGFR-transfected 32D (32D-EGFR) cell line was reported as a suitable EGFR pathway inhibitor screening system based on interleukin-3 (IL-3) and EOF dependent cell survival (Lin et al. 2008, *Anal Biochem*. 377, 89-94).

SUMMARY

One embodiment of invention provides an antibody against human epidermal growth factor receptor (EGFR), comprising an amino sequence as set forth in SEQ ID No. 3.

One embodiment of the invention provides a fusion protein comprising said antibody fused with an Fc region of human IgG as a bivalent antibody.

One embodiment of the invention provides a fusion protein comprising said antibody fused with a collagen scaffold as a trivalent antibody.

One embodiment of the invention provides a fusion protein comprises said antibody fused with a heavy chain variable region ($V_H$) displace light chain variable region ($V_L$) form of human IgG as a tetravalent antibody.

One embodiment of the invention provides a pharmaceutical composition comprising said antibody or fusion proteins for treatment of diseases or symptoms induced from the EGFR overexpression.

One embodiment of the invention provides a imaging agent comprising said antibody and a labeling agent binding to said antibody.

One embodiment of the invention provides a method for cell labeling, comprising: providing a labeling agent binding to said antibody and mixing the labeling agent with a biosample of interest, wherein the labeling agent binds to cells with EGFR on the cell surface in the biosample to form a complex.

One embodiment of the invention provides a method for screening antibody against human EGFR, comprising: (i) panning phages in an antibody library with cells that are not expressing EGFR, (ii) selecting phages obtained from the said Step (i) through phage display selection with EGFR-expressing cells, (iii) selecting phages obtained from Step (ii) through phage display selection with a recombinant, extracellular domain of EGFR (EGFR-ECD), and (iv) obtaining an antibody against EGFR.

A detailed description is given in the following embodiments with reference to the accompanying drawings.

BRIEF DESCRIPTION OF THE DRAWINGS

The embodiments can be more fully understood by reading the subsequent detailed description and examples with references made to the accompanying drawings, wherein:

FIGS. 3A~3C show a result of nucleotide sequence alignment (SEQ ID NO: 7) between the two variation of EGFR specific domain antibody D2 clones (D2(V1) (SEQ ID NO: 1) & D2(V2) (SEQ ID NO: 2)) according to one embodiment.

DETAILED DESCRIPTION

Figure 1A:
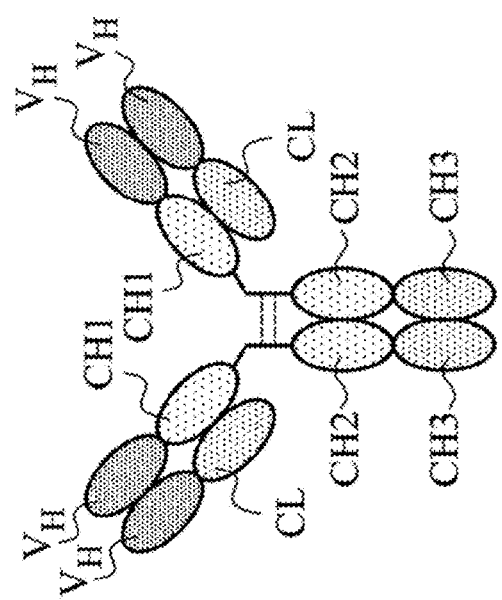
FIG. 1A shows a schematic structure of the fusion protein dAb-D2-hFc in one example of the present invention, in which the $V_H$ region represents the antibody according to one embodiment and the CH2 and CH3 represent Fc regions of human IgG.

In the following detailed description, for purposes of explanation, numerous specific details are set forth in order to provide a thorough understanding of the disclosed embodiments. It will be apparent, however, that one or mote embodiments may be practiced without these specific details. In other instances, well-known structures and devices are schematically shown in order to simplify the drawing Specifically, the antibody according to embodiments of the present invention comprises an amino acid sequence as set forth in SEQ ID No. 3 or an amino acid sequence encoded by the nucleotide sequence as set forth in SEQ ID No. 1. The antibody according to embodiments of the present, invention may also comprise the amino acid sequence SEQ ID No. 3 with a substitution of tyrosine (Tyr) for aspartic acid (Asp) at position 117 as set forth in SEQ ID No. 4 or an amino acid sequence encoded by the nucleotide sequence as set forth in SEQ ID No. 2.

According to embodiments of the invention, the antibody has activity to specifically bind to the human epidermal growth factor receptor (EGFR), resulting in inhibition of the EGFR overexpression in abnormal health conditions. In addition, when fusing with Fc fragments of human IgG, the antibody can be readily introduced into cells by endocytosis and, thus, easily in vivo bind to EGFR.

The antibody according to embodiments of the present invention is obtained from a novel screening method. The screening method, briefly, comprises the following steps: (i) panning phages in an antibody library with cells that are not expressing EGFR, (ii) selecting phages obtained from Step (i) through phage display selection with EGFR-expressing cells, (iii) selecting phages obtained from Step (ii) through phage display selection with a recombinant extracellular domain of the EGFR (EGFR-ECD), and (iv) obtaining an antibody against EGFR.

The term "cells that are not expressing EGFR" herein refers to a cell that is not specifically expressing EGFR during cell cycle, such as mouse IL-3 dependent 32D cell (Alimandi et al., 1997, *EMBO J.* 16, 5608-17). In one example of the present invention, phages recorded in a human domain antibody library were first panned by mouse 32D cells that were not expressing EGFR in nature to exclude the phages binding to the mouse 32D cells. Thereafter, like FIG. 2B, the remaining phages preceded the first and second rounds of phage display selection with the EGFR-transfected mouse 32D (32D-EGFR) cells, and the selected phages further preceded the third and fourth rounds of phage display selection with the recombinant extracellular domain of EGFR (EGFR-ECD). The resultant single domain antibody (dAbs) showed specific binding ability to human EGFR (positive result in ELISA analysis) with high phage titers, indicating that the method for screening antibodies against human EGFR is reliable.

The term "phage display selection" herein refers to a method for antibody selection through phage display. Phage display is based on genetic modification of coat proteins of filamentous bacteriophages such as M13 used in *E. coli*. Protein or peptide fused to phage coat proteins are displayed on surface of phage that bind to the target molecular of interest. Due to the use of phage display selection, the method for screening antibody according to the present invention can avoid the conventional method to construct specific antibody library derived from animal immunization.

Figure 2A:
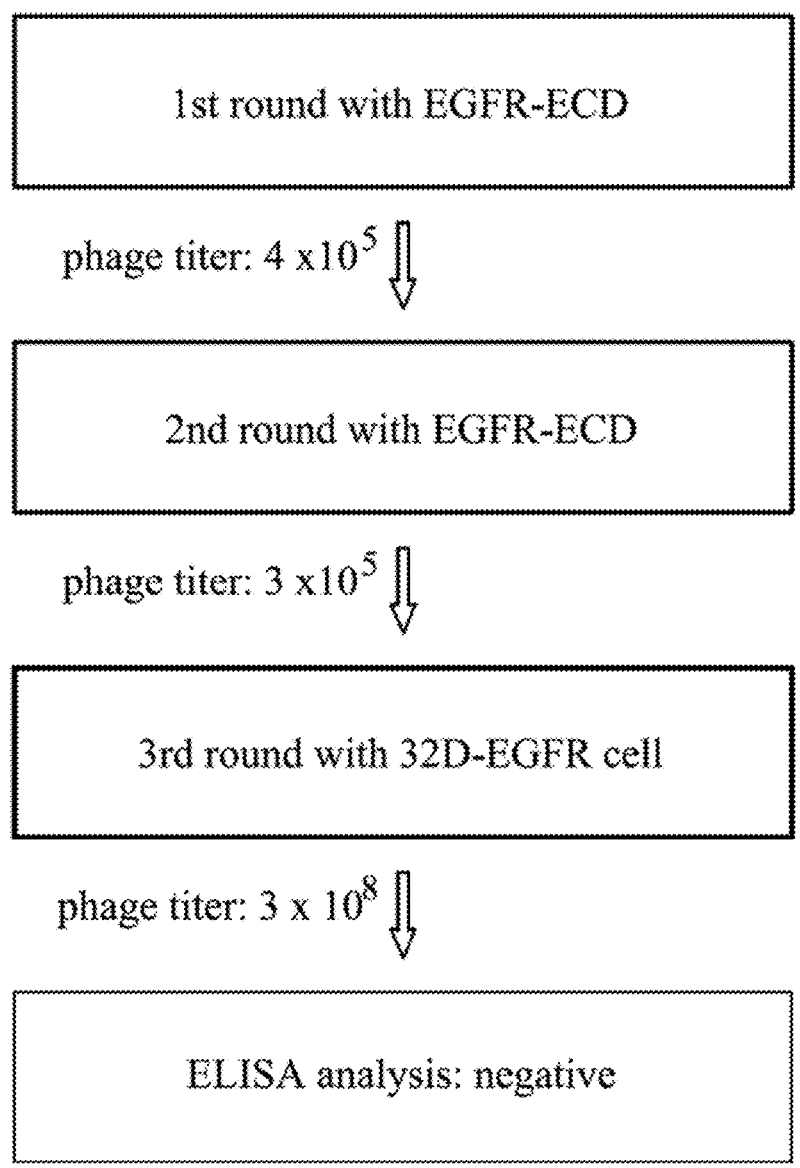
FIG. 2A shows a strategy for antibody selection through phage display selection by using EGFR specific extracellular domain (EGFR-ECD) and 32D-EGFR cells sequentially.
Figure 2B:
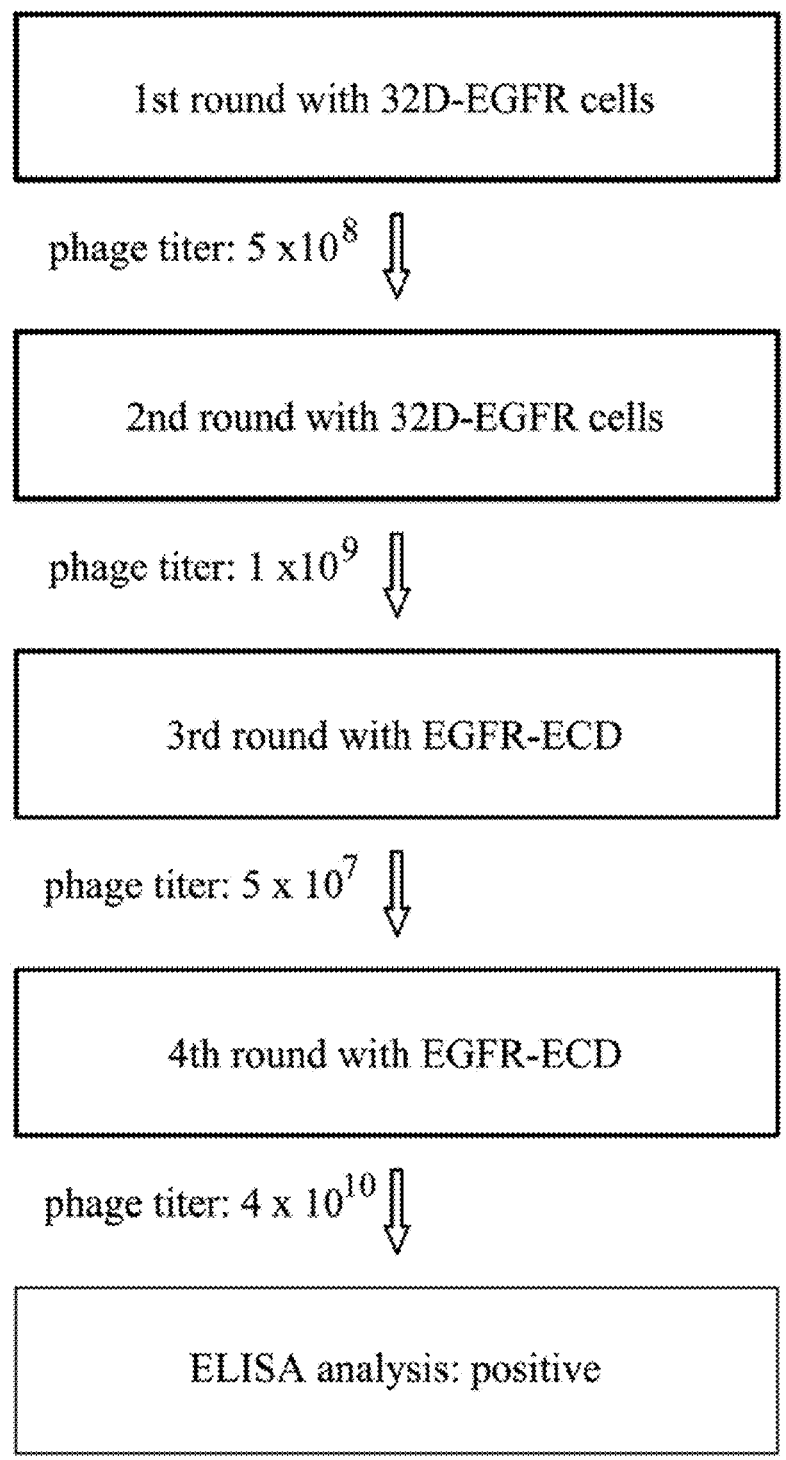
FIG. 2B shows one example of the present invention for antibody selection through phage display selection by using 32D-EGFR cells and EGFR-ECD sequentially.

According to embodiments of the present invention, a high phage titer can be obtained by performing the first two rounds of phage display selection with EGFR-transfected cells and at least two rounds of phage display selection with EGFR-ECD (FIG. 2B). The phage titer shown in FIG. 2B was more than the effective level, $1 \times 10^8 \sim 1 \times 10^9$ cfu/ml, indicating that the concentration of the antibody selected by the method was enough to show binding specificity. In addition, the selected antibody did not lose the EGFR-binding specificity (a positive result in ELISA analysis).

Comparatively, a conventional antibody selection based on phage display selection was performed in the EGFR-ECD. The phage titer of the conventional selection after two rounds of selection was far from the effective level ($<1 \times 10^6$ cfu/ml), and the selected antibody after three rounds of selection lost its activity of specifically binding to EGFR (a negative result in ELISA analysis) (FIG. 2A). In other words, the method according to the present invention is more effective and reliable than conventional ones.

In the method for screening antibody according to embodiments of the invention, the rounds of phage display selection by using the EGFR-ECD can be performed for at least two rounds in Step (iii), but it is not limited thereto. According to the example of the present invention described in the followings, a phage titer with more than $10^{10}$ cfu/ml was observed after two rounds of the EGFR-ECD phage display selection. It is reasonable to expect that the phage titer will not largely decrease even after several rounds of the same selection. Note that concerning the operation limit of phage display selection, two to six rounds of phage display selection is preferable.

According to embodiments of the invention, the antibody may further fuse to a fragment crystallizable (Fc) region of human IgG to form a fusion protein. In this example, the antibody consisting of the amino acid sequence as set forth in SEQ ID No. 3 (dAb-D2) was fused with the Fc region of human IgG as set forth in the amino acid sequence of SEQ ID No. 6 to form a fusion protein, dAb-D2-hFc. Alternatively, a construct that expresses the dAb-D2-hFc fusion protein can be constructed by the nucleotide sequence as set forth in SEQ ID No. 1 with the nucleotide sequence of the human IgG Fc region as set forth in SEQ ID No. 5. The schematic structure is like FIG. 1A, in which the $V_H$ refers to dAb-D2 and CH2 and CH3 refers to the Fc region of human IgG to form a bivalent antibody. The term "bivalent antibody" refers to an antibody that has two variable regions for binding to antigens and thus, a bivalent antibody theoretically has nearly a 2-fold binding affinity of a monovalent one. However, due to the physical structure or chemical property of the antibody, the binding affinity of a bivalent antibody may not show the theoretical folds. In embodiments of the invention, the bivalent fusion protein dAb-D2-hFc shows an increased binding affinity to EGFR than the antibody dAb-D2 which binding activity is too low and could not calculate the binding affinity.

Figure 1B:
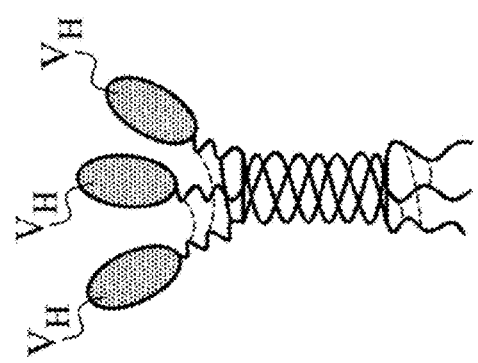
FIG. 1B shows a schematic structure of the fusion protein in one example of the present invention, in which the $V_H$ region represents the antibody according to one embodiment and the spiral structure represents collagen scaffold.

In another example, the antibody according to embodiments of the present invention may fuse with a collagen scaffold. The schematic structure is like FIG. 1B, wherein $V_H$ refers to dAb-D2, and the spiro-structure refers to collagen scaffold. The fusion protein is trivalent due to the polymerization of the collagen scaffold. The term "trivalent antibody" refers to an antibody that has three variable regions for binding to antigens, and thus, a trivalent antibody theoretically has nearly a 3-fold binding affinity of a monovalent one. However, due to the physical structure or chemical property of the antibody, the binding affinity of the trivalent antibody may not show the theoretical folds. The property of the collagen scaffold and protocol of antibody fused with the collagen scaffold can be found in Fan et al. 2008, *FASEB J.* 22, 3795-3804, which is incorporated herein for reference.

Figure 1C:
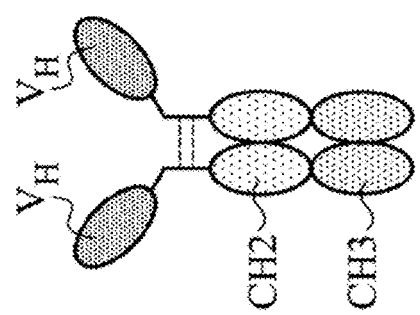
FIG. 1C shows a schematic structure of the fusion protein $V_H$-dAb-D2×4-Ig in one example of the present invention, in which the $V_H$ region represents the antibody according to one embodiment and the CH1, CH2, CH3 and CL represent a $V_H$ displace $V_L$ form of human IgG.

In another example, the antibody according to embodiments of the present invention may fuse with $V_H$ displace $V_L$ form of the human IgG to form a tetravalent fusion protein ($V_H$-dAb-D2×4-Ig). The schematic structure is like FIG. 1C, wherein $V_H$ refers to dAb-D2, and CH1, CH2, CH3 and CL1 refer to human IgG regions. The term "tetravalent antibody" refers to an antibody that has four variable regions for binding to antigens and thus, a tetravalent antibody theoretically has nearly a 4-fold binding affinity of a monovalent one. However, due to the physical structure or chemical property of the antibody, the binding affinity of the tetravalent antibody may not show the theoretical folds. In this invention, the tetravalent antibody $V_H$-dAb-D2×4-Ig shows a stronger binding affinity to EGFR than the bivalent antibody dAb-D2-hFc, indicating that the antibody binding affinity was enforced through increasing the antibody valence. The tetravalent fusion protein may be produced according to the disclosure of US Patent Publication No. US 20060083747, which is incorporated herein for reference.

According to embodiments of the present invention, the antibody is applicable to diseases and symptoms induced by EGFR overexpression. Based on the binding specificity of the antibody of the present invention to the EGFR, the EGF-EGFR binding in nature can be decreased so as to relieve or cure the diseases and symptoms induced from EGFR overexpression. Accordingly, the antibody of the present, invention can be an active ingredient in a pharmaceutical composition, which is effective on treatment of the diseases and symptoms induced from EGFR overexpression, such as non-small-cell carcinoma (NSCLC), squamous cell carcinoma (SCC), head and neck cancer, breast cancer, prostate cancer, ovary cancer, or the like.

The pharmaceutical composition according to embodiments of the present invention may be in a dosage form of pellets, capsules, film-coated tablets, effervescent tablets, granules, powders, suspensions, syrups, or the like, with pharmaceutically acceptable carriers and additives. The pharmaceutically acceptable carriers and additives may be excipients, antioxidants, emulsions, dispersions, bacteriostatic agents, flavors, edible pigments, buffers, solvents, pH modulators, surfactants, or the like. The pharmaceutical composition according to the present invention may be administrated individually or in combination with other drugs. The route of administration may be oral, subdermal, transdermal intravenous, or the like. The dosage may depend on patient ages, weights, health condition, disease types, disease development, affected location or other factors and be determined according to the routines in the field by relevant practitioners.

In one example, the antibody of embodiments of the invention may be conjugated or fused with a labeling agent for the use of imaging agents. The labeling agent may comprise color materials or radioactive materials. The term "color material" refers to a substance that changes in colors in vitro or in vivo, such as: fluorochromes, like fluorescein isothiocyanate (FITC), Alexa Fluor dyes, Cyanine dyes (C2, Cy3 and Cy5); fluorescent proteins, like phytochrome-based near-infrared fluorescent protein (iRFP) (Miao et al. 2010, *J Biomed Opt.* 15, 036007); bioluminescences, like firefly luciferase (Fluc) or *Gaussia* luciferase (Gluc) (Venisnik et al. 2007, *Mol Imaging Biol.* 9, 267-77); nanoparticles, like quantum dots, iron oxide magnetic beads or superparamagnetic iron oxide beads (Olafsen et al. 2010, *Semin Nucl Med.* 40, 167-181) (Yang et al. 2009, *Small.* 5, 235-43). The term "radioactive material" herein refers to a substance with radioactive property in vitro or in vivo, such as $^{90}Y$, $^{111}In$, $^{131}I$ or the radioactive material routinely used in pharmaceutical applications. The labeling agent may be adequately used for in vitro, in vivo or ex vivo according to the properties of the labeling agent, such as cell fluorescence or luminescence, quantitative positron emission tomography (PET) or magnetic resonance imaging (MRI). A labeling agent binding to the antibody of embodiments of the present invention can specifically bind to the EGFR, and the cell carrying the EGFR on the surface would therefore be labeled. Accordingly, the embodiments of invention further comprises a method of cell labeling, comprising: providing a labeling agent binding to the antibody of the embodiments of present invention, and mixing the labeling agent with a biosample of interest, wherein the labeling agent binds to cells with the EGFR on the surface in the biosample to form a complex. Based on the binding specificity between the EGFR and the antibody of embodiments of the present invention, the method can specifically mark cells carrying EGFR on the surface and easily identify the cells.

EXAMPLE

Materials and Methods

Materials

A Human Domain Antibody Library (DAb library) (cat no: DAB1000) was purchased from Source Bioscience Life-Sciences, Dulbecco's modified Eagle's medium (DMEM), RPMI-1640 medium, penicillin, streptomycin and L-glutamine were purchased from Life Technologies Corporation. Fetal bovine serum (FBS) was purchased from the Thermo Scientific HyClone, WEHI-3 conditioned medium which contained IL-3 was generated from a filtered culture medium of WEHI-3 cells which were cultured in a DMEM medium supplemented with 10% FBS. A recombinant extracellular domain of the EGFR (EGFR-ECD, cat no: 100-15R) was purchased from PeproTech.

Cell Lines

Human epithelial carcinoma cell line A431 were cultured in a DMEM supplemented with 10% FBS plus penicillin (50 U/ml) and streptomycin (50 mg/ml) at 37° C. in 5% $CO_2$ atmosphere. Murine hematopoietic cell line 32D and 32D-EGFR were cultured in an RPMI-1640 medium supplemented with 10% FBS, 5% WEHI-3 conditioned medium, L-glutamine (2 mM) plus penicillin (50 U/ml) and streptomycin (50 mg/ml) at 37° C. in 5% $CO_2$ atmosphere.

Methods

Phage Rescue, Titration and Preparation:

Phage titers were determined by infection of eluted phage into log-phase *Escherichia coli* TG1. Eluted phages were amplified by infection of *E. coli* TG1 with a KM13 helper phage for a next round selection according to manufacture's protocol. After overnight growth at 25° C. new amplified phages were purified and concentrated from a bacterial supernatant with poly ethylene glycol 6000 (PEG6000) and resuspended in 1.5 ml PBS for a next round selection or used in A431 cell-based ELISA screening.

Example 1

Phage Display Selection Via Combination of the EGFR-ECD and 32D-EGFR Cells

A ~100 kDa recombinant extracellular domain of the EGFR (EGFR-ECD) comprising 621 amino acids was used as target protein during selections. For each round of selection, a Nunc-Immuno MaxiSorb tube was coated overnight with 6 µg/ml recombinant EGFR-ECD in PBS at 4° C. with gentle agitation. Tubes were washed three times with a PBS buffer and ~$5 \times 10^{12}$ cfu/ml of polyclonal phages in 4 ml a StartingBlock blocking buffer were added to the tube and incubated for 1.5 h at room temperature with gentle agitation. The tube was washed ten times with PBS containing 0.1% Tween 20 (PBST wash buffer) and two times with PBS. Binding of phage were eluted with 4 ml trypsin solution for 1 h at room temperature with gentle agitation. The eluted phages were amplified, titrated and prepared as described above. Two rounds selection were performed. After two rounds selection on EGFR-ECD, one additional round selection on 32D-EGFR cells was performed. 32D cells and 32D-EGFR cells growing on a 15-cm culture dish were washed twice in PBS buffer. To deplete the non-specific phage from the human domain antibody library, $8 \times 10^6$ cell/ml of the 32D cells were incubated with $5 \times 10^{12}$ cfu/ml of phages in 2 ml of serum-free DMEM medium supplemented with 2.5% BSA for 1 h at room temperature with gentle agitation. 32D cells were pelleted by centrifugation at 1,500 rpm and the supernatant was recovered. $4 \times 10^6$ cell/ml of the 32D-EGFR cells were incubated with 32D cells depleted phage library for 1.5 h at room temperature with gentle agitation. 32D-EGFR cells were subsequently washed twice in a cold PBS buffer, 32D-EGFR cells pellet were resuspended in 1 ml of trypsin solution and were incubated for 30 min at room temperature to elute the phages from the cell membrane. The eluted phages were amplified, titrated and prepared as described above. A polyclonal phage titer was too low after two runs selection on EGFR-ECD. After the third round selection on 32D-EGFR cells, the recovered phage titer was over $10^8$, but no positive results from the following A431 cell-based ELISA assay. These results indicated selection on EGFR-ECD at the first two runs was not a good approach (FIG. 2A).

Example 2

Phage Display Selection Via Combination of 32D-EGFR Cells and EGFR-ECD

For each round of selection, 32D and 32D-EGFR cells growing on a 15-cm culture dish were washed twice in a PBS buffer. To deplete the non-specific phage from the human domain antibody library, the 32D cells in a concentration of $8 \times 10^6$ cell/ml were incubated with $5 \times 10^{12}$ cfu/ml of phages in 2 ml of serum-free DMEM medium supplemented with 2.5% BSA for 1 h at room temperature with gentle agitation. 32D cells were pelleted by centrifugation at 1,500 rpm and the supernatant was recovered. The 32D-EGFR cells in a concentration of $4 \times 10^6$ cell/ml were incubated with the 32D cell depleted phage library for 1.5 h at room temperature with gentle agitation. The 32D-EGFR cells were subsequently washed twice in a cold PBS buffer. The 32D-EGFR cells pellet were resuspended in 1 ml of trypsin solution and were incubated for 30 min at room temperature to elute the phages from cell membrane. The eluted phages were amplified, titrated and prepared as described above. Two rounds selection were performed. After two rounds selection on 32D-EGFR cells, additional two rounds selection of the EGFR-ECD was performed. For each round of selection, a Nunc-Immuno MaxiSorb tube was coated overnight with 6 µg/ml of the recombinant EGFR-BCD in PBS at 4° C. with gentle agitation. Tubes were washed three times with a PBS buffer and ~$5 \times 10^{12}$ cfu/ml of polyclonal phage in 4 ml Starting-Block blocking buffer was added to the tube and incubated for 1.5 h at room temperature with gentle agitation. The tube was washed ten times with a PBS containing 0.1% Tween 20 (PBST wash buffer) and two times with PBS. Binding of phage were eluted with 4 ml trypsin solution for 1 h at room temperature with gentle agitation. The eluted phages were amplified, titrated and prepared as described above. After two runs selection on 32D-EGFR cells, the recovered phage titer increased with each round of selection. After the following two runs selection on EGFR-ECD, the recovered phage titer was more than $10^{10}$ cfu/ml (FIG. 2B). These results indicated that selection on the 32D-EGFR cells at the first two runs was a good approach when compared with the EGFR-ECD (FIGS. 2A and 2B).

Example 3

Isolation and Characterization of Monoclonal EGFR Specific Antibody

After total four rounds of selection comprised of two different screening strategies, individual clones from the series dilution were tested for antigen binding by A431 cell-based ELISA and EGFR-ECD based ELISA. The EGFR overexposing A431 cells in a concentration of $4 \times 10^5$ cell/ml were seeded in Corning CellBIND 96-well plate for 16-24 h before assay. After PBS wash, the A431 cells were fixed with BD CytoFix fixation buffer for 15-20 min at room temperature. After fixation and PBS wash procedure, A431 cells were blocked with StartingBlock blocking buffer for 30 min at 37° C. Plates were washed three times with PBST wash buffer and 2-fold diluted monoclonal amplified phage in 50 µl Starting-Block blocking buffer was added to each well and incubated for 1 h at room temperature. Wells were washed five times with PBST wash buffer. Binding phage antibodies were detected with HRP-conjugated anti-M13 antibody diluted 1:5000 in StartingBlock blocking buffer and TMB as substrate.

EGFR-ECD was also used for further re-confirmation of the phage display selection results. Nunc MaxiSorb 96-well plate were coating overnight with 6 µg/ml of the recombinant EGFR-ECD in PBS at 4° C. Plates were washed three times with PBST wash buffer and 2-fold diluted monoclonal amplified phage in 50 µl StartingBlock blocking buffer was added to each well and incubated for 1 h at room temperature, Wells were washed five times with PBST wash buffer. Binding phage antibodies were detected with HRP-conjugated anti-M13 antibody diluted 1:5000 in StartingBlock blocking buffer and TMB as substrate.

Figure 3B:
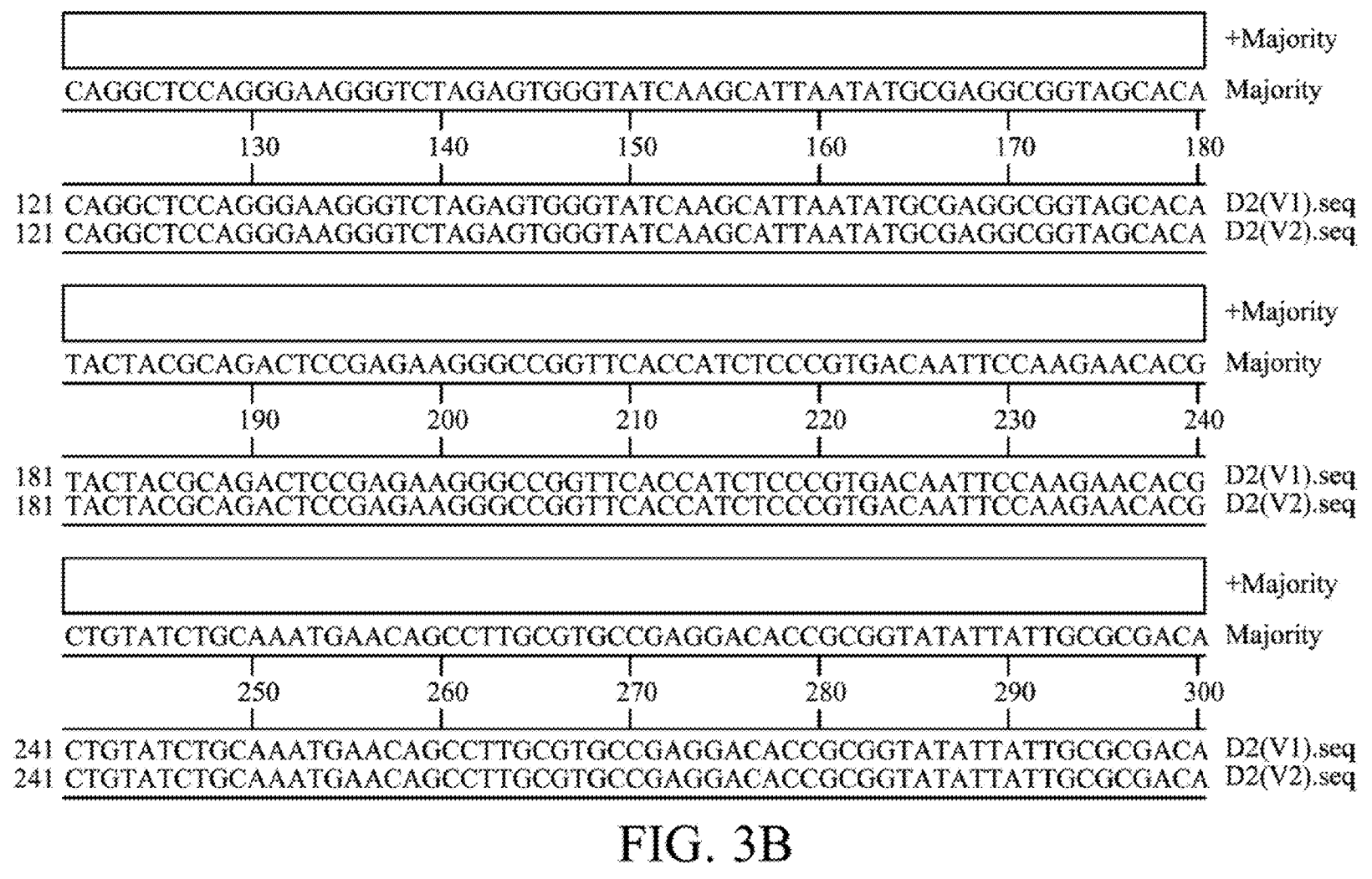

More than 56% positive results (53/93) were obtained from A431 cell-based ELISA and 29 positive clones were selected for further re-confirm. As expected, 100% positive results (29/29) were obtained from EGFR-ECD based ELISA, ELISA-positive clones from the fourth selection cycle were sequenced. Analysis of sequences led to the identification of one unique sequence, D2 clone, which contains nucleotide variants, V1 and V2 (FIGS. 3A~3C). The amino acid sequence of the nucleotide variant V1 of D2 clone (D2(V1)) was represented as SEQ ID No. 3, and the nucleotide sequence encoding the amino acid sequence was listed in SEQ ID NO. 1. The amino acid sequence of the nucleotide variant V2 of D2 clone (D2(V2)) was represented as SEQ ID No. 4, which is the amino acid sequence SEQ ID No. 3 with a substitution of tyrosine (Tyr) with aspartic acid (Asp) at position 117. The nucleotide sequence encoding the amino acid sequence SEQ ID No. 3 was listed in SEQ ID NO. 2.

Example 4

Expression and Purification of Recombinant dAb-D2-hFc

Figure 4:
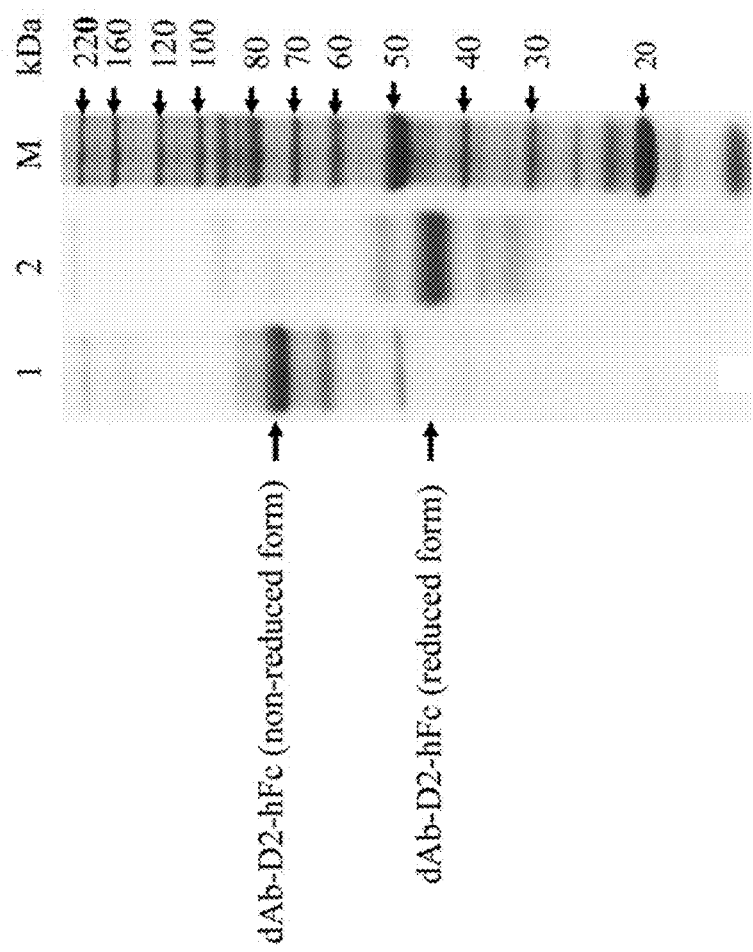
FIG. 4 shows the reduced form and non-reduced form of the fusion protein dAb-D2-hFc according to one embodiment.

A dimeric form of recombinant dAb-D2-hFc was constructed by fusing dAb-D2 (SEQ ID NO. 1) to the Fc of human IgG1 (SEQ ID NO. 5). The dAb-D2-hFc was obtained by stable transfection of expression, constructs in Chinese hamster ovary (CHO) cell line (RIKEN Bio Resource Center, Japan) using QIAGEN Effectene transaction reagent according to the manufacturer's instructions. The stable clones were selected in the presence of 400 μg/ml Invitrogen Hygromycin B. Clone stably expressing dAb-D2-hFc were identified via A431 cell-based ELISA assay and HRP-conjugated anti-human Fc antibody (1:10,000 dilution) as the detection agent. dAb-D2-hFc was purified from the filtered culture medium using GE protein A affinity chromatography. The purity of the dAb-D2-hFc was confirmed by SDS-PAGE analysis under reducing and non-reducing conditions. This result indicated that the molecular weight of dAb-D2-hFc fusion protein was about 80 kDa (FIG. 4).

Example 5

Figure 5:
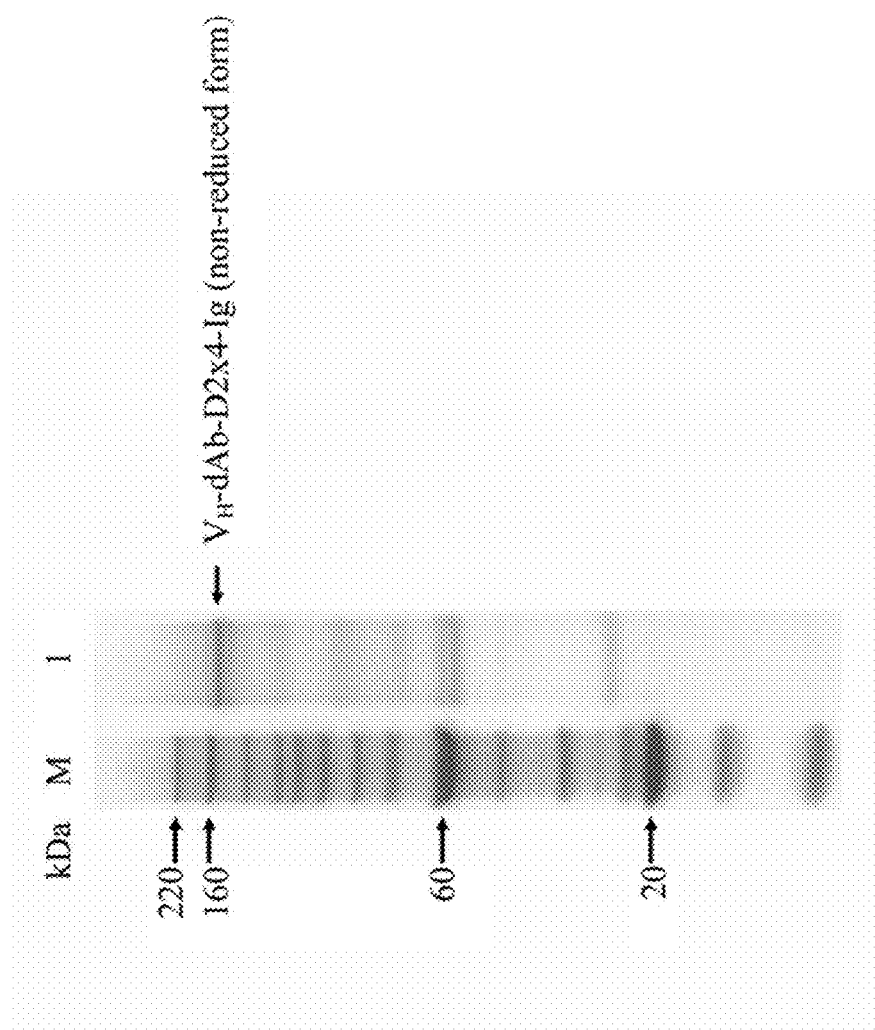
FIG. 5 shows the non-reduced form of the fusion protein $V_H$-dAb-D2×4-Ig according to one embodiment.

Expression and Purification of Recombinant $V_H$-dAb-D2×4-Ig Tetrameric Antibody The recombinant $V_H$-dAb-D2×4-Ig tetrameric antibody was constructed by fusing with the heavy chain variable region ($V_H$) displace light chain variable region ($V_L$) form of human IgG, in which the $V_H$ was dAb-D2 (SEQ ID No. 1). The $V_H$-dAb-D2×4-Ig-expressing vector was transfected into Chinese hamster ovary (CHO) cell line (RIKEN Bio Resource Center, Japan) using QIAGEN Effectene transfection reagent according to the manufacturer's instructions. The stable clones were selected in the presence of 400 μg/ml Invitrogen Hygromycin B. Clone stably expressing $V_H$-dAb-D2×4-Ig were identified via A431 cell-based ELISA A assay and HRP-conjugated anti-human Fc antibody (1:10,000 dilution) as the detection agent. $V_H$-dAb-D2×4-Ig was purified from the filtered culture medium using GE protein A affinity chromatography. The non-reduced form of the $V_H$-dAb-D2×4-Ig was confirmed by SDS-PAGE analysis. This result indicated that the molecular weight of $V_H$-dAb-D2×4-Ig fusion protein was about 160 kDa (FIG. 5)

Example 6

Determination of Antibody Binding Affinity

Figure 6:
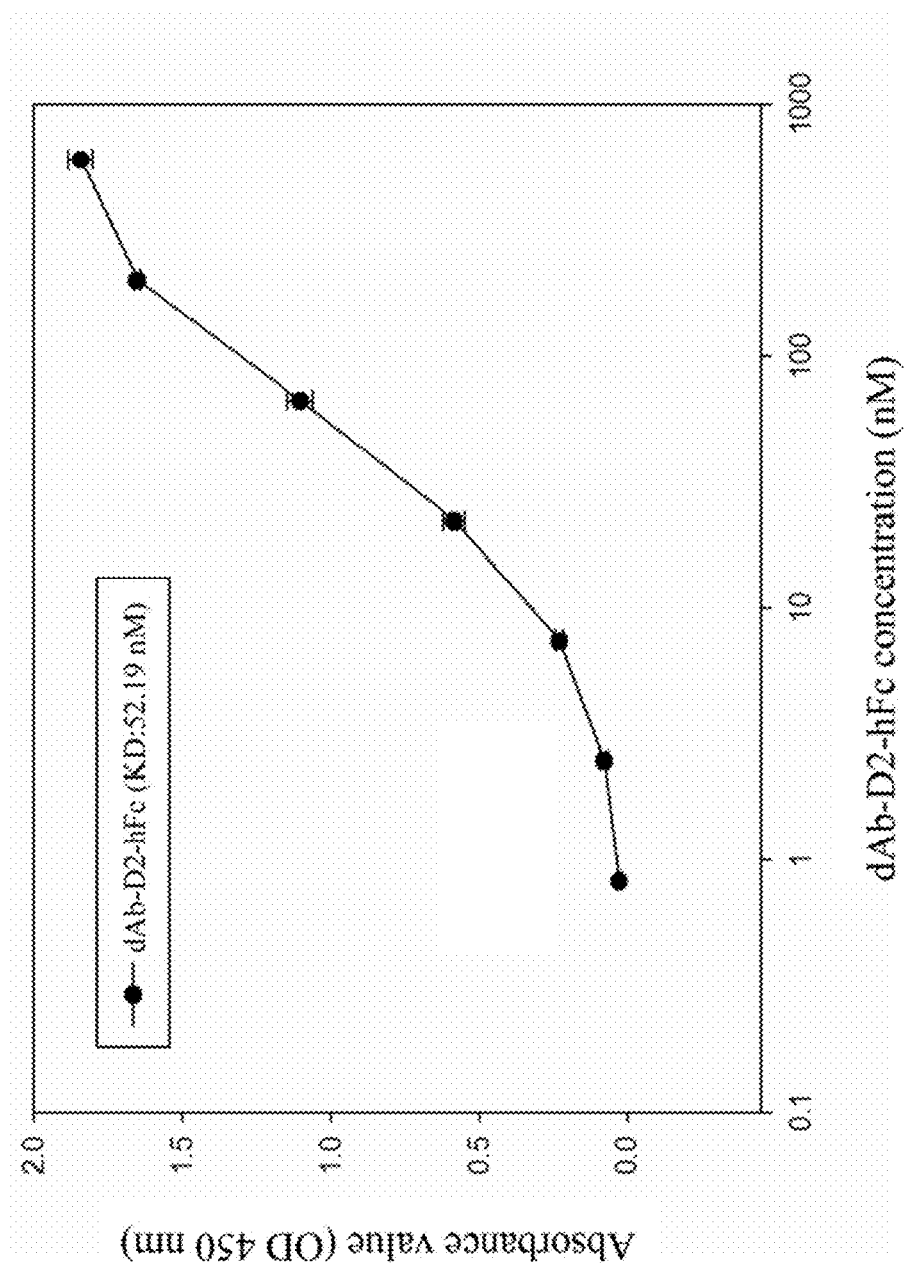
FIG. 6 shows the binding affinity of the fusion protein dAb-D2-hFc to A431 cells according to one embodiment.
Figure 7:
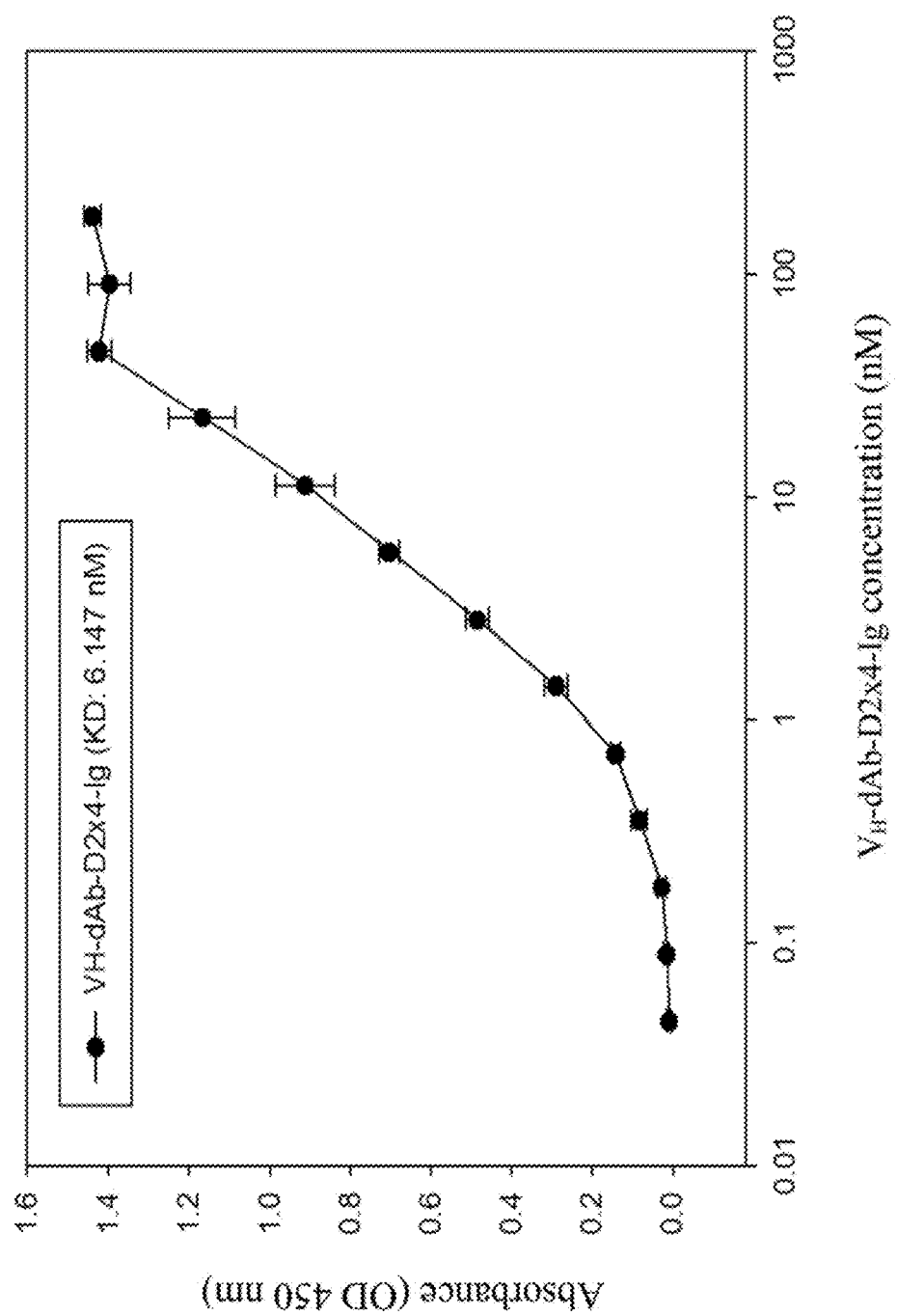
FIG. 7 shows the binding affinity of the fusion protein $V_H$-dAb-D2×4-Ig to A431 cells according to one embodiment.

A431 cells in a concentration of $4 \times 10^5$ cell/ml were seeded in Corning CellBIND 96-well plate for 16-24 h before assay. After PBS wash, the A431 cells were fixed with BD CytoFix fixation buffer for 15-20 min at room temperature. After fixation and PBS wash procedure, the A431 cells were blocked with StartingBlock blocking buffer for 30 min at 37° C. Plates were washed three times with PBST wash buffer and incubated with the indicated concentrations of dAb-D2-hFc and $V_H$-dAb-D2×4-Ig in 50 ul StartingBlock blocking buffer on ice for 1.5 h. Wells were washed three times with PBST wash buffer. After washing, the plate was incubated with HRP-conjugated anti-human Fc antibody diluted 1:10,000 in StartingBlock blocking buffer on ice for 1 hour. Plates were washed and incubated with TMB. Absorbance at 450 nm was read on a microplate reader. After SigmaPlot software analysis, the dissociation equilibrium constant ($K_D$) value of dAb-D2-hFc and $V_H$-dAb-D2×4-Ig fusion protein was about 52 nM and 6 nM, respectively, (FIGS. 6 and 7).

Example 7

Antibody Internalization Assay

Figure 8:
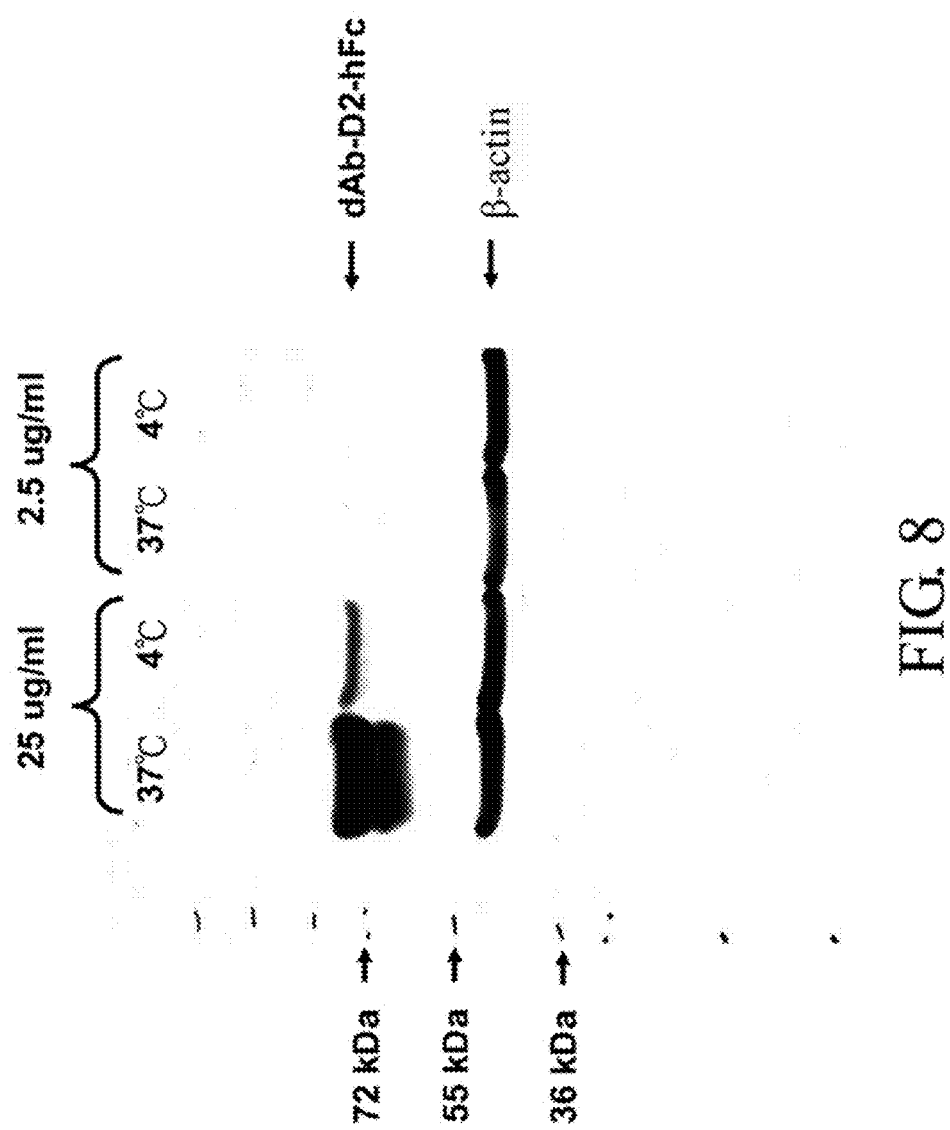
FIG. 8 shows endocytotic activity of the fusion protein dAb-D2-hFc in A431 cells according to one embodiment.
Figure 9:
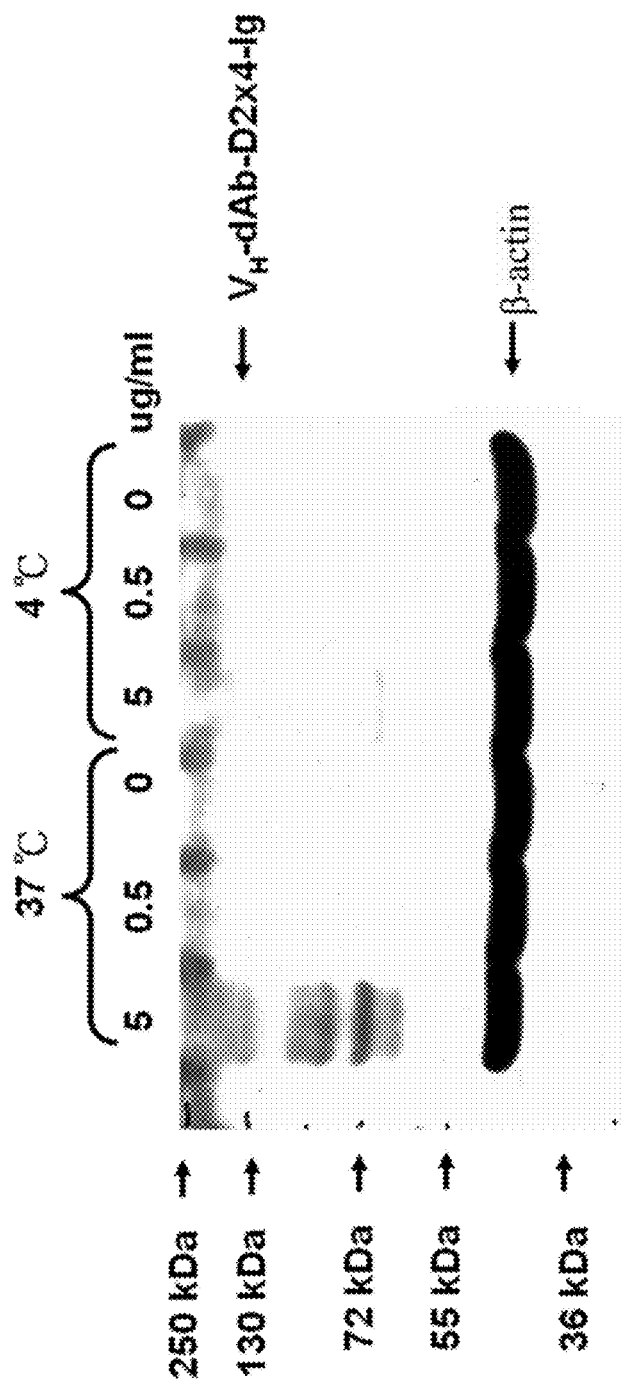
FIG. 9 shows endocytotic activity of the fusion protein $V_H$-dAb-D2×4-Ig in A431 cells according to one embodiment.

A431 cells growing on a 15-cm culture dish were removed by Invitrogen TrypLE™ Select and wash twice in cold PBS buffer. Indicated concentrations of the dAb-D2-hFc and $V_H$-dAb-D2×4-Ig recombinant protein in serum-free medium were incubated with $1 \times 10^6$ cell/ml of A431 cells at 37° C. or on ice for 30 min. After PBS buffer washing, membrane bound protein were remove via TrypLE™ Select, treatment at 37° C. for 10 min. After treatment, A431 cell pellet were lysed in Sigma CelLytic™ M lysis buffer and equal amounts of cell lysates from each sample were used for Western blot analysis. Internalized dAb-D2-hFc and $V_H$-dAb-D2×4-Ig were respectively detected via HRP-conjugated anti-human Fc antibody (diluted 1:10,000 in StartingBlock blocking buffer) and β-actin (diluted 1:5,000 in StartingBlock blocking buffer) as the internal control. The internalization was temperature dependent, so that we can observe more internalized dAb-D2-hFc and $V_H$-dAb-D2×4-Ig fusion protein in 37° C. condition than that on ice (FIGS. 8 and 9). This result confirmed internalized activity of dAb-D2-hFc and $V_H$-dAb-D2×4-Ig fusion protein.

Example 8

Growth Inhibition of Cancer Cell Line

Figure 10:
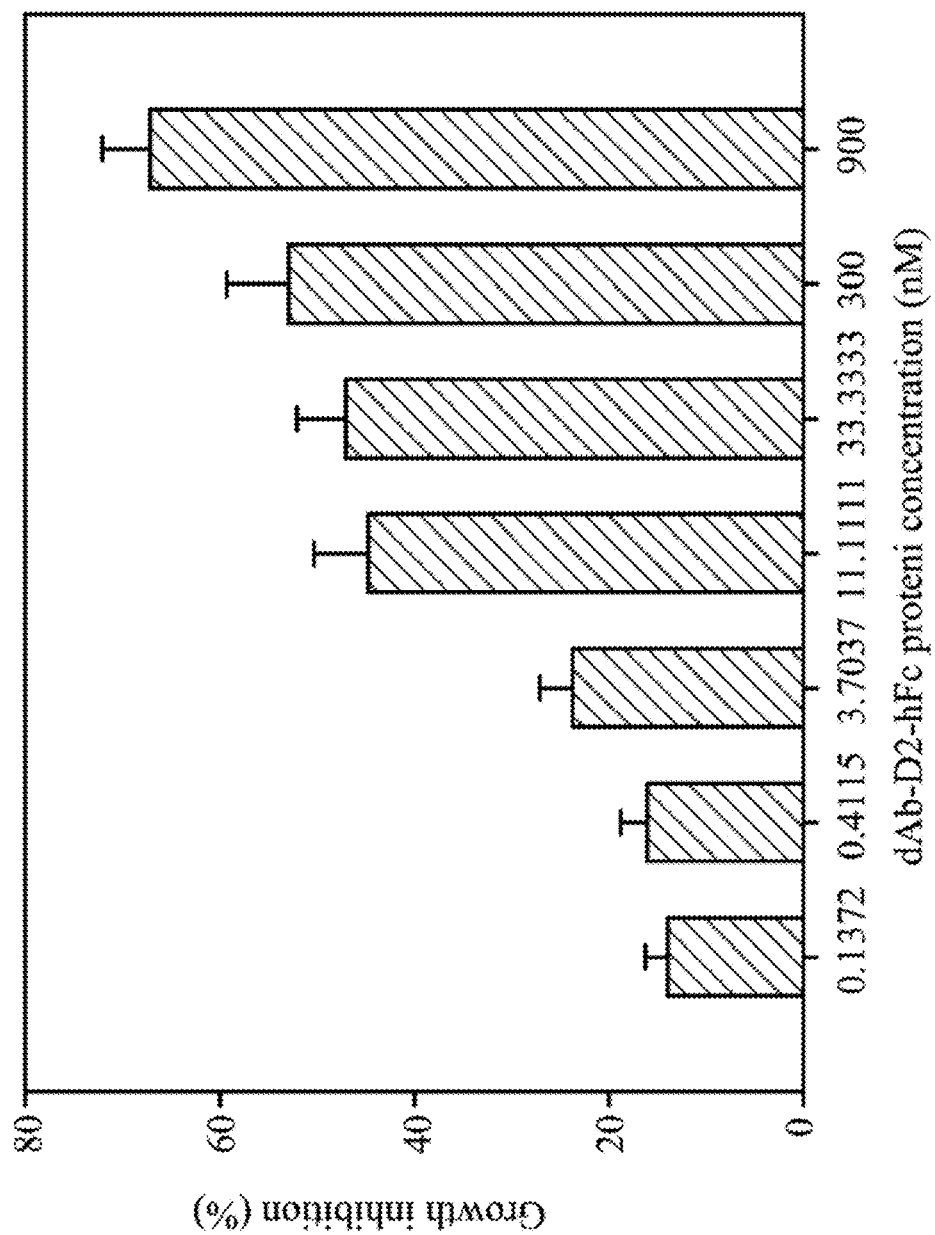
FIG. 10 shows the effect of the fusion protein dAb-D2-hFc on A431 cell growth according to one embodiment.
Figure 11:
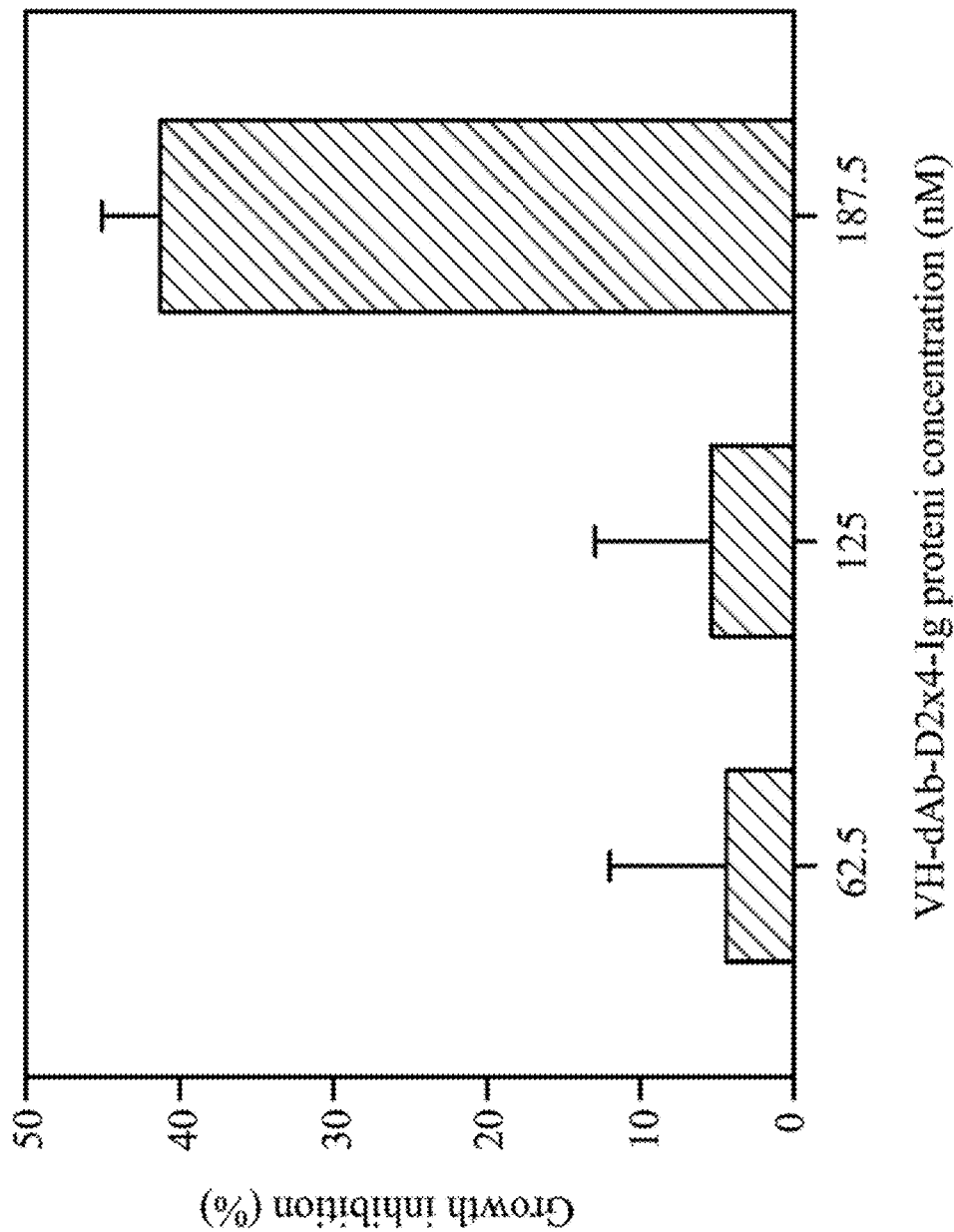
FIG. 11 shows the effect of the fusion protein $V_H$-dAb-D2× 4-Ig on A431 cell growth according to one embodiment.

The cell growth inhibition of A431 cells was evaluated by Invitrogen PrestoBlue™ cell viability reagent. In brief, $2 \times 10^4$ cell/ml of A431 cells were seeded in Corning 96-well cell culture plate for 16-24 h before assay. Cells were treated with the indicated concentrations of dAb-D2-hFc and $V_H$-dAb-D2×4-Ig in culture with 0.5% FBS for 5 days. At the end of the 5 days incubation period with the dAb-D2-hFc and $V_H$-dAb-D2×4-Ig, the cells were incubated with 20 μl of PrestoBlue reagent in each well of 96-well plates for 2 h at 37° C. Cell growth was measured using Multi-Well Plate Reader with excitation, at 544 nm and emission at 590 nm. This result indicates dAb-D2-hFc and $V_H$-dAb-D2×4-Ig fusion protein could inhibit A431 cell proliferation in a dose-dependent manner (FIGS. 10 and 11).

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. An anti-human epidermal growth factor receptor (EGFR) antibody, comprising the amino acid sequence as set forth in SEQ ID No. 3.

2. An anti-human epidermal growth factor receptor (EGFR) antibody, comprising the amino acid sequence as set forth in SEQ ID No. 4.

3. The antibody as claimed in claim 1, wherein the amino acid sequence is encoded by the nucleotide sequence as set forth in SEQ ID No. 1.

4. The antibody as claimed in claim 2, wherein the amino acid sequence is encoded by the nucleotide sequence as set forth in SEQ ID No. 2.

5. A fusion protein, comprising the antibody as claimed in claim 1 fused with an Fc region of human IgG, wherein the fusion protein specifically binds to human EGFR.

6. The fusion protein as claimed in claim 5, wherein the fusion protein is bivalent.

7. A pharmaceutical composition, comprising the antibody as claimed in claim 1 being an active ingredient, for treatment of diseases or symptoms induced from EGFR overexpression.

8. A pharmaceutical composition, comprising the fusion protein as claimed in claim 5 being an active ingredient, for treatment of diseases or symptoms induced from EGFR overexpression.

9. An imaging agent, comprising the antibody as claimed in claim 1 and a labeling agent binding to the antibody.

10. The imaging agent as claimed in claim 9, wherein the labeling agent comprises a color material or radioactive material.

11. The imaging agent as claimed in claim 10, wherein the color material comprises fluorochromes, fluorescent proteins, bioluminescences, quantum dots, iron oxide magnetic beads or superparamagnetic iron oxide beads.

12. The imaging agent as claimed in claim 11, wherein the fluorochromes comprise fluorescein isothiocyanate (FITC), Alexa Fluor dyes or Cyanine dyes (C2, Cy3 and Cy5).

13. The imaging agent as claimed in claim 11, wherein the fluorescent proteins comprise phytochrome-based near-infrared fluorescent proteins (iRFP).

14. The imaging agent as claimed in claim 11, wherein the bioluminescences comprise firefly luciferases (Fluc) or *Gaussia* luciferases (Gluc).

15. The imaging agent as claimed in claim 10, wherein the radioactive material comprises 90Y, 111In or 131I.

* * * * *